United States Patent
Nishida et al.

(10) Patent No.: US 6,630,517 B2
(45) Date of Patent: *Oct. 7, 2003

(54) PROCESS FOR HYDROLYZING AND RECYCLING A POLYURETHANE

(75) Inventors: Satoshi Nishida, Osaka (JP); Osamu Kato, Osaka (JP); Yoshiyuki Nagase, Kobe (JP); Ryuichi Fukuzato, Osaka (JP); Masahiro Yamagata, Osaka (JP); Katsuhisa Kodama, Nishinomiya (JP); Terukazu Matsuda, Takatsuki (JP); Shigetoshi Suzuki, Ibaraki-ken (JP); Takao Naito, Shimizu (JP)

(73) Assignees: Kabushiki Kaisha Kobe Seiko Sho, Kobe (JP); Takeda Chemical Industries, Ltd., Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/355,338
(22) PCT Filed: Feb. 4, 1998
(86) PCT No.: PCT/JP98/00450
§ 371 (c)(1), (2), (4) Date: Oct. 7, 1999
(87) PCT Pub. No.: WO98/34904
PCT Pub. Date: Aug. 13, 1998

(65) Prior Publication Data
US 2003/0012710 A1 Jan. 16, 2003

(30) Foreign Application Priority Data
Feb. 5, 1997 (JP) .............................. 9-022998
May 9, 1997 (JP) .............................. 9-119798

(51) Int. Cl.[7] .................................................. C08J 11/04
(52) U.S. Cl. ....................................................... 521/49
(58) Field of Search ..................... 521/49, 49.5, 40, 521/40.5; 422/187–190, 901, 131, 139; 564/414, 305

(56) References Cited

U.S. PATENT DOCUMENTS

| | | | | |
|---|---|---|---|---|
| 2,937,151 A | * | 5/1960 | Broeck et al. | 521/164 |
| 3,128,310 A | | 4/1964 | Koch | 564/414 |
| 3,143,515 A | * | 8/1964 | Hurley | 521/49 |
| 3,225,094 A | * | 12/1965 | Wolf | 260/570 |
| 3,300,417 A | * | 1/1967 | McElroy | 521/49.5 |
| 3,331,876 A | | 7/1967 | Van Horn et al. | 564/414 |
| 3,404,103 A | * | 10/1968 | Matsudaira et al. | 521/49.5 |
| 3,738,946 A | * | 6/1973 | Frulla et al. | 428/903.3 |
| 4,025,559 A | * | 5/1977 | Johnson | 564/393 |
| 4,051,212 A | | 9/1977 | Grigat et al. | 264/102 |
| 4,110,266 A | * | 8/1978 | Sheratte | 521/167 |
| 4,137,266 A | | 1/1979 | Cassata | 564/414 |
| 4,267,078 A | * | 5/1981 | Lidy et al. | 260/2.3 |
| 4,281,197 A | * | 7/1981 | Oblinger | 564/393 |
| 4,328,368 A | | 5/1982 | Salloum et al. | 564/393 |
| 4,605,762 A | * | 8/1986 | Mandoki | 540/451 |
| 4,654,443 A | | 3/1987 | Marks et al. | 564/305 |
| 4,970,342 A | * | 11/1990 | Fauss et al. | 564/393 |
| 5,300,530 A | * | 4/1994 | Machado et al. | 521/49 |
| 5,386,055 A | | 1/1995 | Lee et al. | 562/512.2 |
| 5,656,757 A | * | 8/1997 | Jenczewski et al. | 540/540 |
| 6,255,529 B1 | * | 7/2001 | Nagase et al. | 210/205 |

FOREIGN PATENT DOCUMENTS

| | | |
|---|---|---|
| CA | 583 372 | 9/1959 |
| EP | 0 219 035 | 4/1987 |
| EP | 0 854 165 A1 * | 7/1998 |
| GB | 1 047 101 | 3/1964 |
| GB | 991387 | 5/1965 |
| JP | 39-006667 | 5/1964 |
| JP | 42-010634 | 6/1967 |
| JP | 43-021079 | 9/1968 |
| JP | 49-090377 | 8/1974 |
| JP | 50-142501 | 11/1975 |
| JP | 51-095027 | 8/1976 |
| JP | 54-070377 | 6/1979 |
| JP | 54-130525 | 10/1979 |
| JP | 55-133336 | 10/1980 |
| JP | 58-049341 | 3/1983 |
| JP | 58-201751 | 11/1983 |
| JP | 59-007141 | 1/1984 |
| JP | 59-016858 | 1/1984 |
| JP | 5-31000 | 2/1993 |
| JP | 9-151270 | 10/1997 |

OTHER PUBLICATIONS

U.S. patent application Ser. No. 09/355,338, filed Aug. 5, 1999, pending.
U.S. patent application Ser. No. 09/410,029, filed Oct. 1, 1999, pending.

* cited by examiner

Primary Examiner—Edward J. Cain
Assistant Examiner—Katarzyna Wyrozebski Lee
(74) Attorney, Agent, or Firm—Oblon, Spivak, McClelland, Maier & Neustadt, P.C.

(57) ABSTRACT

A process for hydrolyzing and recycling polyurethanes as target compounds to be hydrolyzed into raw materials or derivatives thereof for the target compounds, comprising bringing pressurized water in a liquid state at a temperature of 190 to 370° C. into contact with the target compounds in a reactor to hydrolyze the target compound; followed by post-processings, such as dewatering, addition, distillation, separation, and liquid separation for a hydrolyzed reaction product discharged from the reactor.

21 Claims, 8 Drawing Sheets

PROCESS FOR HYDROLYZING AND RECYCLING A POLYURETHANE

TECHNICAL FIELD

The present invention relates to an apparatus for and process of hydrolyzing and recycling polyisocyanate derivatives, such as polyurethane resins used in wide applications including furniture, bedding, vehicles, heat insulating materials for building material and consumer electronics, shoe soles and the like, and oligomers of isocyanate compounds in distillation residues discharged in a chemical plant as by-products. Such polyisocyanate derivatives are brought into contact with water heated to high temperature and pressurized to a liquid state, thereby being hydrolyzed and recovered as raw material compounds or derivatives thereof for the target compound. In the present invention, "polyisocyanate derivatives" indicate derivatives having at least one isocyanato group and/or group derived from an isocyanato group, and include wide variety of compounds from low molecular weight compounds to polymers.

BACKGROUND ART

In Japan, about 400,000 tons of polyurethane resins are produced in the form of soft, semi-hard, and hard urethane foams, elastomers, and Reaction Injection Moldings (RIM), and are used in various fields. Recently, public awareness of environmental protection have been heightened in all over the world, and under such a situation, studies to develop processes for recycling various kinds of plastics, including polyurethane resins, have been carried out.

Known processes for recycling polyurethane resins are roughly classified in the following categories: 1) a material recycling technique; 2) a chemical recycling technique; and 3) an energy recycling technique. In the material recycling technique 1), polyurethane resins are subjected to a physical treatment such as crushing without changing their physical properties. The crushed polyurethane resins are subjected to thermal press molding or adhesion press molding into new products, or utilized as fillers for extruded products, RIM products, concrete and the like. In the chemical recycling technique 2), polyurethane resins are recovered to raw materials or chemical substances usable as raw materials. Known as chemical recycling techniques are a glycol decomposition method, an amine decomposition method, a hydrolysis method and the like. In the energy recycling method 3), polyurethane resins are utilized as energy resources. Specifically, polyurethane resins are directly used as fuels or are subjected to treatment for generating steam or fuel gases which are then used as fuels.

The method of the present invention is classified in the chemical recycling technique 2). However, the conventional chemical recycling technique has drawbacks that it requires other compounds such as glycol, amine, and alkali as a decomposing agent, and in addition, it takes long reaction time which renders this technique uneconomical. Due to such drawbacks, there are only a few cases where the conventional chemical recycling technique is actually used for recycling polyurethane resins.

On the other hand, studies have been carried out to develop another chemical recycling technique where polyurethane resins are hydrolyzed into polyol and amine using water as a decomposing agent. For example, Japanese Laid-Open Patent Publication No. 54-70377 discloses a method for decomposing polyurethane in the presence of superheated steam and an alkaline/alkaline earth metal compound at about 300° C. or lower and 0.4 to 10 gauge pressure. In the invention disclosed in Japanese Laid-Open Patent Publication No. 54-70377, the inventors have made various studies to find out a method for hydrolyzing polyurethane by superheated steam. However, at a pressure less than 10 gauge pressure, the reaction rate is low and long time is required for reaction. Therefore, they have concluded in the disclosure that the presence of compound which exhibits an activity as catalyst, such as ammonium and alkali, is necessary.

On top of methods for recycling used polyurethane resins, there are also demands for establishing methods for recycling wastes discharged in a chemical plant as by-products. Such wastes, discharged in a chemical plant as distillation residues at a purifying and distilling step of synthesizing a compound having isocyanato groups, almost always contain oligomers such as dimers and trimers of the aimed compound. However, it is impossible to utilize the oligomers. For example, in a chemical plant producing a diisocyanate compound, a diisocyanate compound having high purity is obtained as a finished product at a purifying and distilling step. Although distillation residues generated at the purifying and distilling step contains a diisocyanate compound, i.e., the aimed compound, the distillation residues cannot be recycled and are disposed of as wastes by incineration and the like. This is because the diisocyanate compound cannot be separated from the oligomers thereof or other impurities.

British patent Publications No. 991387 and No. 1047101, U.S. Pat. Nos. 3,225,094 and 4,137,266 respectively disclose a method for hydrolyzing and recycling isocyanate derivatives where isocyanate derivatives are recycled in the form of amine compounds. As all of these methods are batchwise methods, there are disadvantages that large amount of energy is required for raising and lowering temperature and pressure at a time of batch replacement. In addition, in terms of the scale of equipment, there is a limitation on the treating capacity of isocyanate derivatives. Therefore, these methods are not industrially suitable.

Japanese Laid-Open Patent Publication No. 9-151270 discloses a method for recycling tolylenediisocyanate where tolylenediisocyanate is recovered in the form of trylenediamine. However, there is no sufficient disclosure as to the optimum conditions of hydrolysis and of post-processings.

In view of the above, the present invention is aimed at providing an apparatus for and process of efficiently recycling polyurethane resin and wastes discharged at a production line for producing low molecular weight polyisocyanate compounds on an industrial scale using substantially only water with no presence of any compound as a hydrolyzing agent.

DISCLOSURE OF THE INVENTION

According to the present invention, an apparatus for hydrolyzing and recycling polyisocyanate derivatives having at least one isocyanato group and/or a group derived from an isocyanato group as target compounds to be hydrolyzed into raw materials or derivatives thereof for the target compounds, the apparatus includes: a hydrolyzer for bringing only pressurized water in a liquid state at a temperature of 190 to 370° C. into contact with the target compounds in the reactor to hydrolyze the target compound: and a postprocessor for conducting post-processings such as dewatering, addition, distillation, separation, and liquid separation for a hydrolyzed reaction product discharged from the reactor.

BRIEF DESCRPTION OF DRAWINGS

BEST MODE FOR CARRING OUT THE INVENTION

Figure 1:
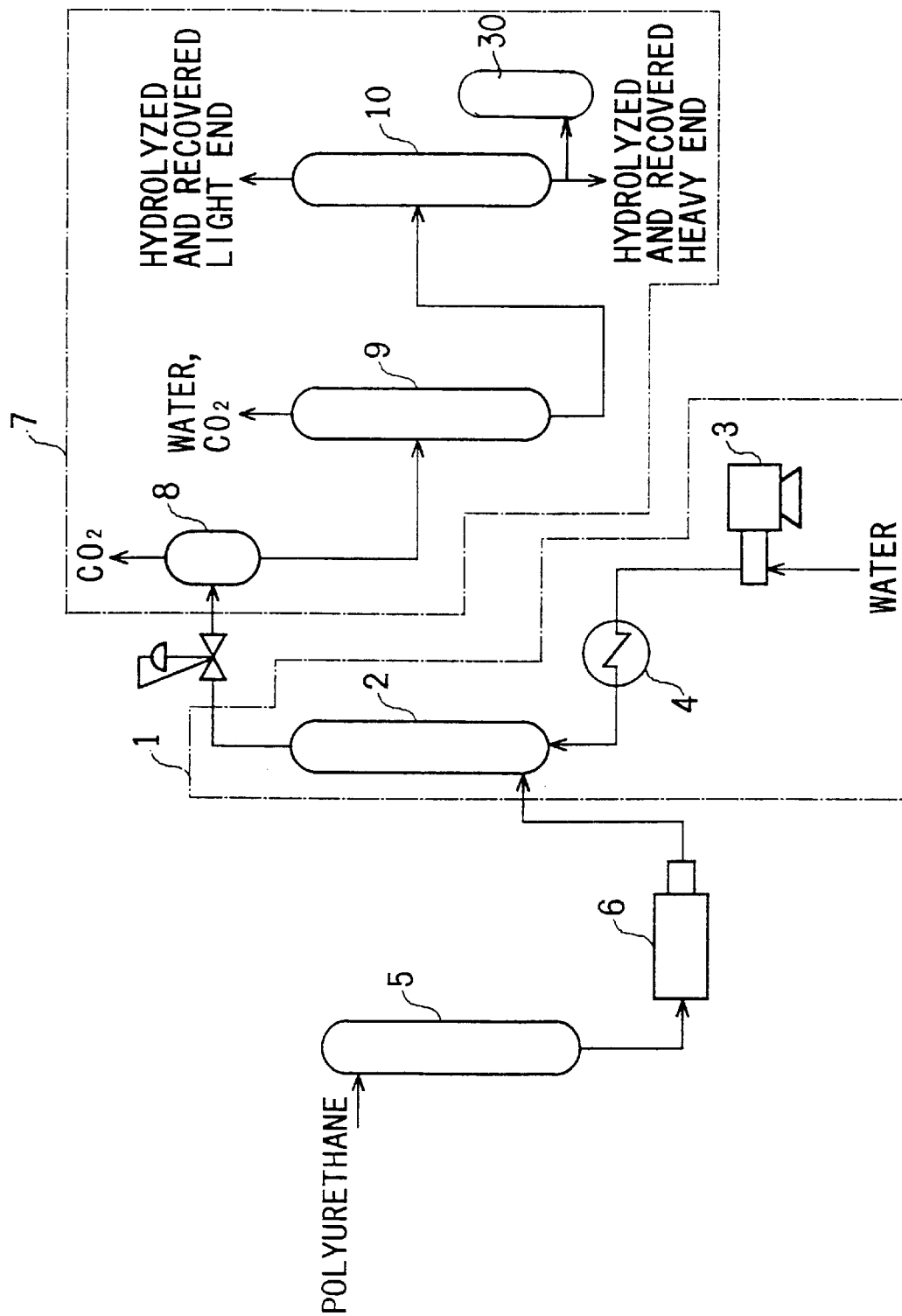
FIG. 1 is a diagram showing a preferable example of the hydrolyzing and recycling apparatus according to the present invention.

The apparatus for hydrolyzing and recycling polyisocyanate derivatives of the present invention is intended for use in hydrolyzing polyisocyanate derivatives having groups derived from isocyanato groups such as polyurethane resins and low molecular weight polyisocyanate compounds into useful and reusable material.

First, target compounds to be treated by the hydrolyzing and recycling apparatus of the present invention will be described.

In the present invention, the target compound to be hydrolyzed means polyisocyanate derivatives having at least one isocyanato group (—NCO) and/or at least one group derived from isocyanato group. The target compound to be hydrolyzed includes, in addition to the compounds having isocyanato groups, compounds having groups (including bonds) derived from isocyanato groups such as urethane bond, allophanate bond, urea bond, biuret bond, amide bond and the like, and an example of such compounds include a polyurethane resin. In addition, also included as an example of such compounds include compounds generated as a result of dimerization or trimerization of the compounds having isocyanato groups. Examples of such compounds include dimers, trimers or oligomers higher than trimers, such as carbodiimide, uretidione, urethane imine, isocyanurate and the like, which are contained in the wastes from a chemical plant producing the compounds having isocyanato groups.

From the viewpoint of recycling, it is preferable to hydrolyze a polyurethane resin or wastes from a chemical plant as a target compound.

Examples of the polyurethane resin used as a target compound include chips or defective products of polyurethane generated at a molding or processing step to produce polyurethane products, wastes of polyurethane products after used in various fields, and the like. Kinds of polyurethane resins include foams such as soft urethane foams, semi-hard urethane foams, hard urethane foams, elastomers (casted, kneaded, or thermoplastic elastomers), RIM products, ISFs (integral skin foams) and the like, all of which can be hydrolyzed by the apparatus of the present invention.

A polyurethane resin is made of a compound having two or more isocyanato groups (polyisocyanate) and generally a compound having active hydrogen (polyol) as main raw materials. However, various polyurethane resins having various physical properties are also available in accordance with the combination of the kinds and the molecular weight of the main raw materials, a catalyst, a chain extension agent, and the like. Specific examples of the raw material of polyurethane resin include tolylenediisocyanate (TDI), modified TDI, diphenylmethanediisocyanate (MDI), polymeric MDI, hydrogenated MDI, modified MDI, hexamethylenediisocyanate (HDI), tolidinediisocyanate (TODI), 1,5-naphthalenediisocyanate (NDI), isophoronediisocyanate (IPDI), p-phenylenediisocyanate, xylylenediisocyanate (XDI), hydrogenated XDI and the like.

Examples of polyol include polyether polyol such as bifunctional, trifunctional, tetrafunctional, hexafunctional, or octafunctional polyetherpolyol derived from alkylene (ethylene or propylene) oxide and initiator having active hydrogen, polytetramethyleneglycol (PTMG), polyester polyol such as condensed-type polyester polyol, lactone-type polyester polyol, and polycarbonate diol, acryl polyl and the like.

The hydrolyzing and recycling apparatus of the present invention can hydrolyze bonds contained in an ordinary polyurethane resin such as urethane bond, allophanate bond, urea bond, biuret bond, and amide bond regardless of the molecular structure of the polyurethane resin and the kinds of units constituting the polyurethane resin. As a result of the hydrolysis, a raw material of the polyurethane resin which is a target compound to be hydrolyzed or the derivatives usable as a raw material of the polyurethane resin, that is, polyol and/or a polyamine compound corresponding to a raw material polyisocyanate, can be recovered.

There may be some cases where polyol and amine, which are hydrolyzed reaction products, are hard to be separated from each other depending on the polyurethane resin. In such a case, it is preferable that a mixture of polyol and amine is subjected to addition reaction with ethylene oxide or propylene oxide to recover polyether polyol. In this manner, there is no need to forcedly separate polyol and amine from each other. Rather, polyether polyol is more preferable, because it is directly usable as a raw material of polyurethane, and as a result, the number of post processes and recycling costs are decreased.

On the other hand, the relatively low molecular weight compound having isocyanato groups or groups derived from isocyanato groups can be recovered as an amine compound having amino groups (—NH$_2$) by hydrolysis.

Typical examples of isocyanate compounds for general purpose and amine compounds recovered by the hydrolyzing and recycling apparatus of the present invention are as follows.

phenyl isocyanate→aniline
tolylenediisocyanate (TDI)→tolylenediamine (TDA)
diphenylmethanediisocyanate→diphenylmethanediamine
dianisidinediisocyanate→dianisidinediamine
tridinediisocyanate→tridinedidiamine
naphthalenediisocyanate→naphthalenediamine
hexamethylenediisocyanate→hexamethylenediamine
isophoronediisocyanate→isophoronediamine
metaxylylenediisocyanate→methaxylylenediamine
2,2,4-trimethylhexamethylenediisocyanate→2,2,4-trimethylhexamethylenediamine dimer acid diisocyanate→dimer acid diamine
bisisocyanatemethylcyclohexane→bisaminomethylcyclohexane
isopropylidenebiscyclohexylmethanediisocyanate→isopropylidenebiscyclohexyldiamine
methylcyclohexanediisocyanate→methylcyclohexanediamine Similarly, compounds having groups or bonds derived from isocyanato groups generated by origomelization of the aforementioned isocyanate compounds can be recovered as corresponding amine compounds.

Hereinafter, the characteristics of the hydrolyzing and recycling apparatus of the present invention will be described.

The hydrolyzing and recycling apparatus of the present invention includes:
  a hydrolyzer for bringing substantially only water at 190 to 370° C. in a liquid state at high pressure into contact with a target compound to be hydrolyzed in a reactor, thereby hydrolyzing the target compound; and
  a post-processor for conducting post-processings such as dewatering, addition, distillation, separation, and liquid separation for the hydrolyzed reaction product discharged from the reactor.

In the present invention, water in a liquid state (not in a steam state) at 190 to 370° C. is brought into contact with the target compound to be hydrolyzed, thereby smoothly hydrolyzing the target compound without using any other compounds for promoting hydrolysis.

The hydrolyzer includes a reactor capable of conducting high pressure reaction as an essential component. Preferable examples of the hydrolyzer include (1) a hydrolyzer for simultaneously heating and pressurizing water into a liquid state, and continuously supplying the water to the reactor, and (2) a hydrolyzer for heating water in a reactor under a pressurized condition.

The hydrolyzer (1) is not specifically limited as far as it is capable of introducing water which is heated and pressurized beforehand to the reactor. For example, the hydrolyzer (1) includes a heater and a pump which are located at any position of the water supplying line extending from a water supplying source to the reactor. Either the heater or pump may be located on the reactor side (i.e., on the downstream side).

The hydrolyzer (2) is not specifically limited as far as it is capable of heating and pressurizing water which has been introduced into the reactor. For example, the hydrolyzer (2) may have a structure in which water pressurized by pump and the like is introduced into the reactor having a heater, or may have a structure in which water is introduced into the reactor having a heater and then the volume inside the reactor is diminished by being pressurized with a cylinder and the like under a hermetically sealed state.

The hydrolyzers (1) and (2) may be used in combination in order to maintain the temperature and pressure during hydrolysis is proceeding in the reactor.

The target compound to be hydrolyzed may be supplied to the reactor by batchwise or continuously. For example, in the case of hydrolyzing and recovering a polyurethane resin, a specific amount of polyurethane resin is put into the reactor, and then, is hydrolyzed by the hydrolyzer.

In the case where the target compound to be hydrolyzed is waste such as distillation residue from a chemical plant, it is preferable that the hydrolyzing and recycling apparatus further includes a supplier for continuously supplying the target compound to be hydrolyzed into the reactor. As such waste is continuously discharged, it is wasteful to hydrolyze them batchwise. If a batchwise method is employed, an energy loss is large in raising and lowering temperature and pressure in the reactor at the time of batch replacement. In addition, a reservoir for storing wastes is required, and the change in quality of target compound to be hydrolyzed such as decomposition and polymerization during stored in the reservoir is inevitable. As will be described later, when a compressor for compressing polyurethane foam is included in the hydrolyzing and recycling apparatus, it is also preferable that the apparatus also includes a supplier for continuously supplying the compressed foam into the reactor.

Specific examples of the supplier include pumps, extruder, or pressure accumulators, and the like. Or alternatively, the apparatus may include an extruder having a heater for introducing a target compound to be hydrolyzed in a heated state.

A post-processor conducts post-processings such as dewatering, addition, distillation, separation, liquid separation and the like for hydrolyzed reaction product discharged from the reactor. However, the post-processing is not limited to dewater, addition, distillation, separation, and liquid separation, but also include various other processings conducted for the hydrolyzed reaction product. Specific examples of the processors included in the post-processor are as follows:

A dewatering processor: a processor which includes devices for respectively conducting distillation, contact with a dewatering agent (an agent which adsorbs water), drying, filtration and the like;

An addition processor: a processor which includes a reactor capable of chemical reaction and the like.

A distillation processor: a processor which includes a distillation device capable of conducting distillation, extractive distillation, molecular distillation and the like;

A separation processor: a processor which includes devices respectively capable of degassing, extraction, centrifugation, filtration, squeezing, fractionation and the like; and A liquid separation processor: a processor which includes a liquid separation device.

The above processings may be conducted under reduced or increased pressure. The post-processor may be used alone or in combination.

The hydrolyzing and recycling apparatus of the present invention may include a compressor. A compressor is useful, for example, in the case of treating polyurethane foam as a target compound to be hydrolyzed. As the compressor compresses the foam to a reduced volume, the reactor can be downsized. Preferably, the compressor capable of compressing polyurethane foam while heating the polyurethane foam to 100 to 250° C. is employed. The compressor is capable of compressing not only soft foam but also hard foam to a small volume (i.e., to a large density) while heating the foam to an appropriate temperature. Examples of the compressor include pressurizer having a heater, and an extruder having a heater (single shaft extruder, double shaft extruder and the like). The extruder is preferable as the compressor, because it also has a function as a supplier. In the case of using the pressurizer having a heater as the compressor, a supplier is additionally provided, or a compressed product is introduced into the reactor batchwise.

Hereinafter, a preferable hydrolyzing and recycling apparatus will be described referring to FIGS. 1 to 4, as to the case where the target compound to be hydrolyzed is a polyurethane resin and as to the case where the target compound to be hydrolyzed is a low molecular weight polyisocyanate compound, respectively. It is to be noted that the present invention is not limited to the configurations shown in FIGS. 1 to 4, but modifications thereof in accordance with the scope of the invention are also within the present invention.

(1) In the Case where the Target Compound to be Hydrolyzed is a Polyurethane Resin:

FIG. 1 is a diagram showing an example of a hydrolyzing and recycling apparatus used for continuously conducting hydrolysis. This apparatus is especially useful for hydrolyzing and recycling polyurethane foam.

A hydrolyzer 1 includes a reactor 2, a supplying pump 3 provided between a water supplying source and the reactor 2, and a heater 4. Water in a liquid state which is pressurized by the pump 3 and heated by the heater 4 respectively is continuously supplied to the reactor 2. In the case of using a reactor having a heater, the heater 4 may be eliminated; however, the structure of the reactor becomes complicated. Either the pump 3 or the heater 4 may be located on the reactor side.

Polyurethane is supplied from a reservoir 5 to the reactor 2 through a compressor made of an extruder 6. In this example, the extruder 6 has functions as a supplier and a compressor. Another supplier such as a gear pump may be further provided between the extruder 6 and the reactor 2.

Polyurethane is stored in the reservoir 5. Polyurethane large in size is cut into an appropriate size and is stored in the reservoir 5. The polyurethane is compressed by the extruder 6 while being heated normally at 100 to 250° C. More preferble lower limit of the heating temperature is 120° C., and more preferable upper limit thereof is 180° C. It is preferable to adjust the compressing conditions so that the time required for the heating and compressing is 5 to 60 minutes in accordance with the performance of the extruder. In the case of treating ordinary soft foam, generally the soft foam is heated and compressed so as to have a density of about 300 kg/m$^3$ or more. In the case of treating ordinary hard foam, generally the hard foam is heated and compressed so as to have a density of about 500 kg/m$^3$ or more.

Polyurethane resin products other than foams also may be heated by the extruder 6 and then is supplied to the reactor 2, as is the case of the aforementioned foams. This is because the heated polyurethane resin and the heated and pressurized water are brought into contact with each other in the reactor to cause prompt hydrolysis therebetween with no need of heating the polyurethane resin in the reactor. However, in the case of treating a polyurethane resin having such high hardness that it exhibits no flowability even if being heated, the polyurethane resin is finely crushed and is introduced into the reactor for hydrolysis.

It is preferable that the internal pressure of the reactor 2 is adjusted to 3 to 30 MPa. With low internal pressure, too long time is required for reaction. More preferable lower limit of the internal pressure is 6 MPa. When the internal pressure is adjusted within the aforementioned range, the hydrolyzing rate of polyurethane reaches 100% for a short time, and therefore, there is no need to adjust the internal pressure to higher than 30 MPa. More preferable upper limit of the internal pressure is 25 MPa, and the most preferably 20 MPa.

Weight of water (hydrolysis ratio) to be brought into contact with polyurethane in the reactor 2 is 1.0 time or more the polyurethane, and it is recommended that the hydrolysis ratio is 10.0 times or less. When the hydrolysis ratio exceeds 10.0 times the polyurethane, the reactor is required to have larger size, or longer time and larger energy are required for separating the hydrolyzed reaction product from water in the post-processing step. More preferable upper limit of the hydrolysis ratio is 4.0 times.

It is preferable that the water in the reactor 2 is at 200 to 370° C. (reaction temperature). When the water is at a temperature exceeding 370° C., although the hydrolyzing rate of polyurethane reaches almost 100%, condensation of polyamine and decomposition of polyol are promoted, and as a result, the recovering rate of polyamine and polyol is lowered. More preferable upper limit of water temperature is 340° C. When the water is at a temperature lower than 200° C., the efficiency is lowered because long time is required for hydrolyzing polyurethane. More preferable lower limit of water temperature is 250° C.

The hydrolyzed reaction product is supplied to a post-processor 7. When the target compound is a polyurethane foam, the hydrolyzed reaction product includes polyamine, polyol, water, $CO_2$, unhydrolyzed substances and the like. As there are various kinds of polyurethane foams, and polyurethane foams are made of various polyisocyanates and various polyols, the hydrolyzed reaction product includes polyamine which is a derivative of polyisocyanate used as a raw material of polyurethane foam to be hydrolyzed, and polyol which is also used as a raw material of the polyurethane foam to be hydrolyzed.

In FIG. 1, post-processor 7 includes a degassing device 8, a dewatering column 9, and a separator 10. In the degassing device 8, $CO_2$ generated when various bonds derived from the isocyanato groups in the polyurethane are hydrolyzed into amino groups (—$NH_2$) is removed from the hydrolyzed reaction product. A part of steam is also removed. In the dewatering column 9, $CO_2$ and water are removed. After dewatering, the obtained liquid is discharged from the dewatering column 9 to the separator 10 for separating polyol from polyamine. In the separator 10, a hydrolyzed and recovered light end containing polyamine as a main component and a hydrolyzed and recovered heavy end containing polyol as a main component are separated from each other.

The post-processor 7 may include a plurality of degassing devices 8, dewatering columns 9, and separators 10, and the order in which they are provided is not limited to the positions shown in FIG. 1. In addition, the post-processor 7 may further include a purifier on the downstream of the separator 10.

When polymeric MDI or prepolymer-type polyisocyanate is used as a raw material polyisocyanate of polyurethane resin, polyamine and polyol in the hydrolyzed reaction product are hard to be separated from each other even if using the separator 10, and high cost will be required in an attempt to separate them from each other. In such a case, it is preferable that the post-processor 7 includes another reactor 30 (apart from the reactor 2) instead of the separator 10. To another reactor 30, the resultant liquid discharged after dewatering is supplied, and alkylene oxide is added thereto to form polyethel polyol. As a result, polyamine and polyol can be recovered in a form of polyethel polyol. Polyamine in the discharged liquid works as an initiator for addition reaction, and a reaction in which alkylene oxide such as ethylene oxide or propylene oxide is added to polyol proceeds.

As polyethyl polyol is usable as a raw material of polyurethane, this method is also capable of hydrolyzing a polyurethane resin to recover a raw material of polyurethane resin. In addition, this method is remarkably economical as compared with the case where polyamine and polyol, of which separation is difficult, are forcedly separated from each other. Therefore, it is recommended that the apparatus for hydrolyzing and recycling a polyurethane resin made of polymeric MDI and prepolymer-type polyisocyanate as raw materials includes a post-processor having a reactor capable of addition reaction.

Figure 2:
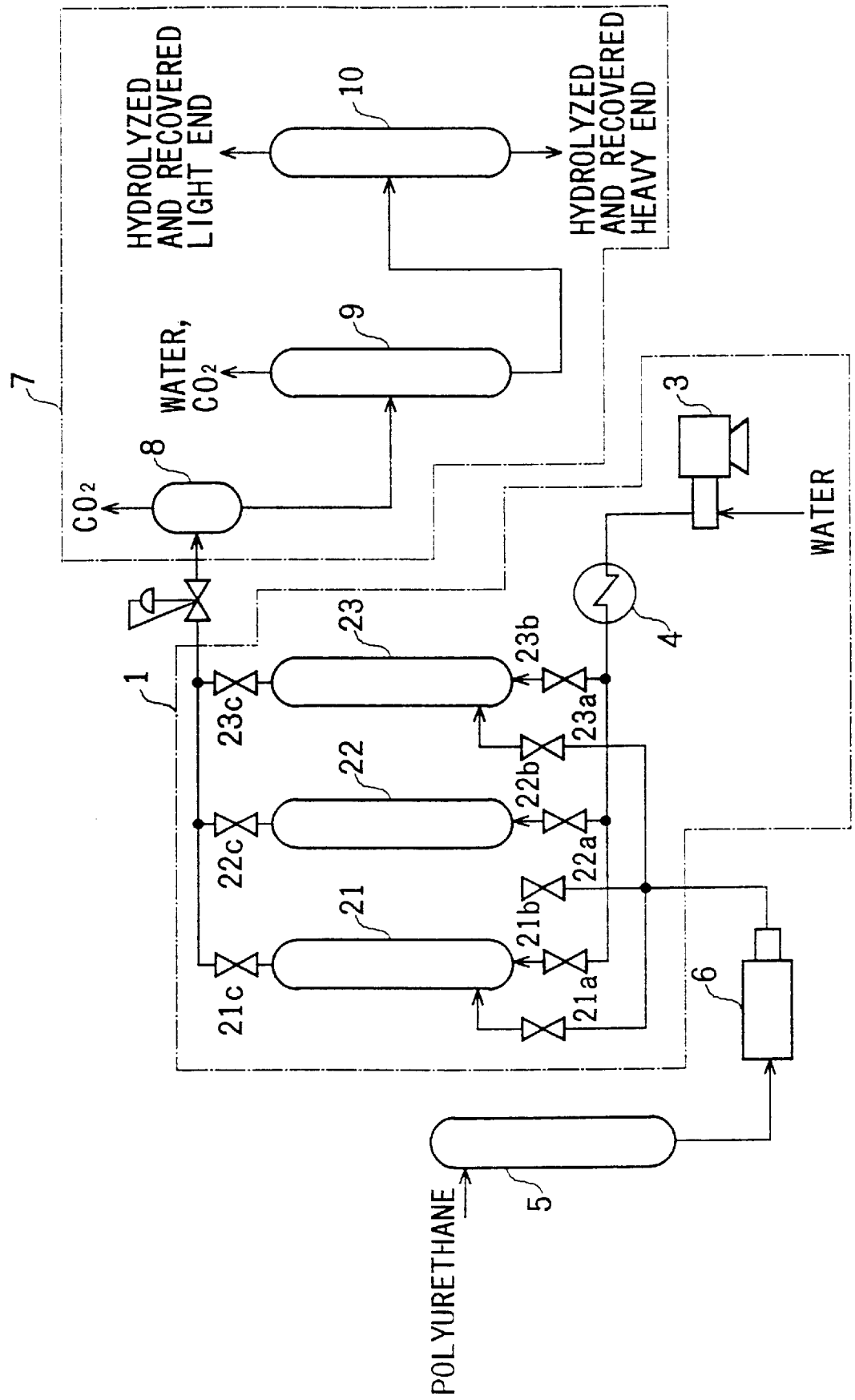
FIG. 2 is a diagram showing another example of the hydrolyzing and recycling apparatus according to the present invention.

FIG. 2 is a diagram showing another example of an apparatus for hydrolyzing and recycling polyurethane resin. A hydrolyzer 1 includes three reactors 21, 22, and 23, a supplying pump 3, and a heater 4. A reservoir 5, an extruder 6, and a post-processor 7 have the same configurations as those of FIG. 1. In this example, after compressing polyurethane, a specific amount of the polyurethane is introduced into the reactor 21. In this case the compressed polyurethane is introduced into the reactor 21 together with heated and pressurized water, or either of them is introduced first and the rest is subsequently introduced. Then, valves 21a and 21b are closed. After the hydrolysis is completed in the reactor 21, a valve 21c is opened to supply the hydrolyzed reaction product to the post-processor 7. After the valves 21a and 21b are closed, that is, after the introduction of water and polyurethane into the reactor 21 is completed, valves 22a and 22b are opened and water and polyurethane are introduced into the reactor 22 to cause hydrolysis. After the hydrolyzed reaction product is supplied from the reactor 21 to the post-processor 7, the hydrolyzed reaction product is supplied from the reactor 22 to the post-processor 7. Similarly, hydrolysis is conducted in the reactor 23, and the hydrolyzed reaction product is supplied to the post-processor 7, while water and polyurethane are introduced into the reactor 21 and 22.

As is the case of example shown in FIG. 2, when a plurality (not limited to three) of reactors are used, hydrolysis and recovering can be conducted batchwise or semi-continuously in a plurality of lines simultaneously. Polyurethane may be introduced batchwise and water may be introduced continuously. In addition, each valve may be configured so that the flow rate is adjustable.

Figure 3:
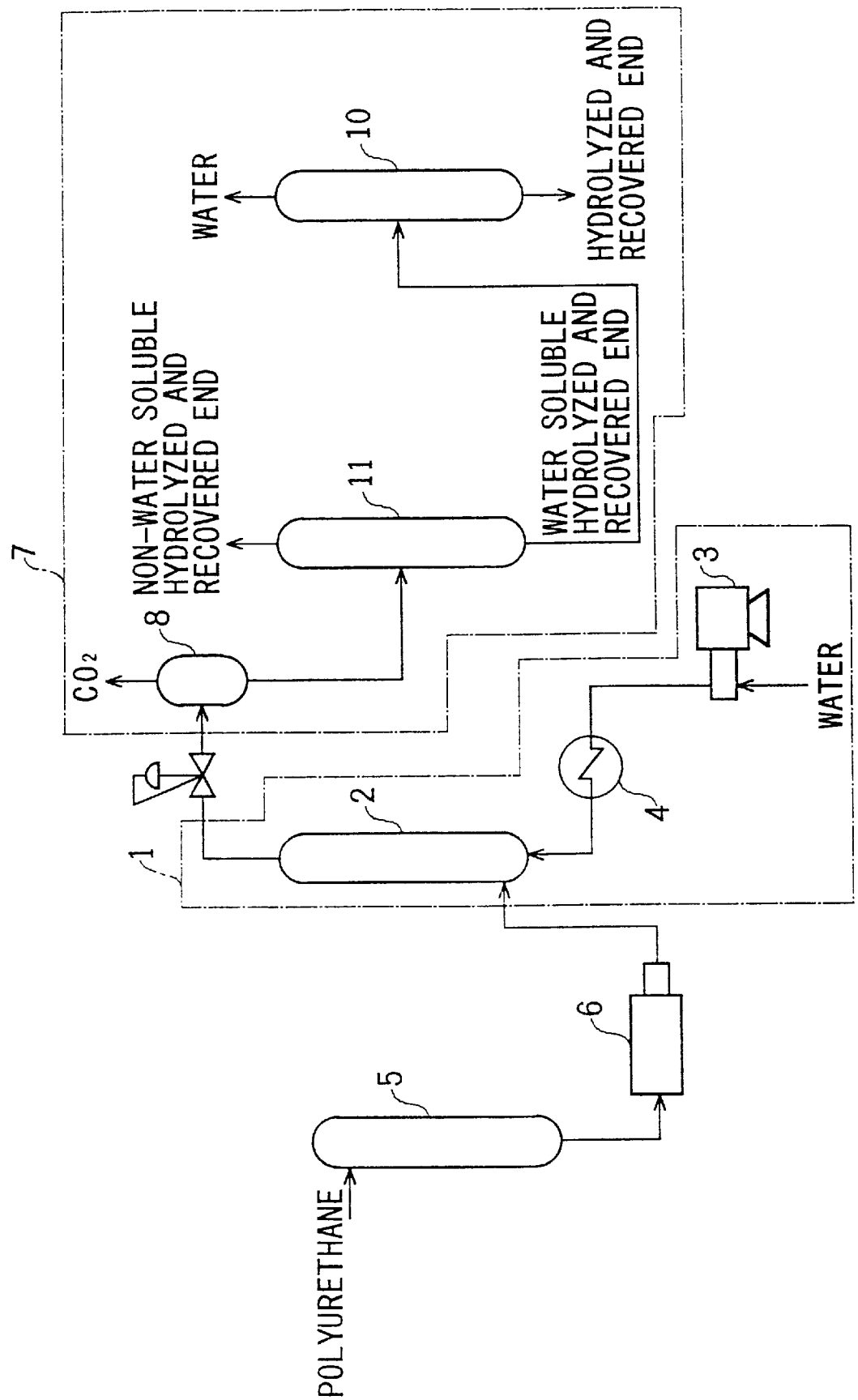
FIG. 3 is a diagram showing still another example of the hydrolyzing and recycling apparatus according to the present invention.

FIG. 3 is a diagram showing the case where a post-processor 7 includes a degassing device 8, a liquid separator 11, and a dewatering column 10. The liquid separator 11 separates a water-soluble hydrolyzed and recovered end and a non-water soluble hydrolyzed and recovered end from each other. Then, the dewatering column 10 dewaters the water-soluble hydrolyzed and recovered end to produce a dewatered hydrolyzed and recovered end. A decanter is preferable as the liquid separator 11.

Figure 4:
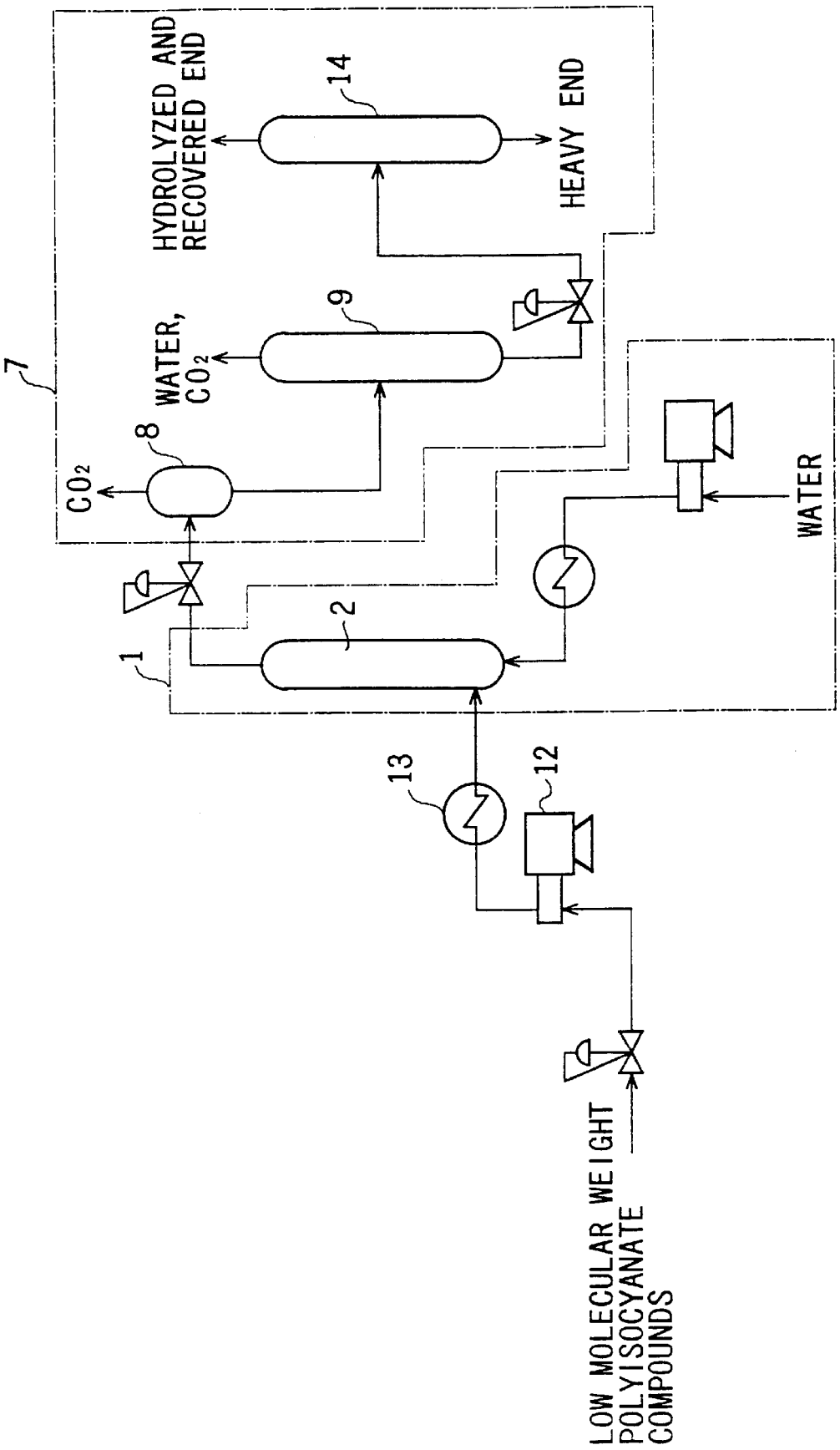
FIG. 4 is a diagram showing still another example of a hydrolyzing and recycling apparatus according to the present invention.

(2) In the Case where the Target Compound to be Hydrolyzed is a Low Molecular Weight Polyisocyanate Compound:

FIG. 4 is a diagram showing an apparatus for hydrolyzing and recycling distillation residues containing low molecular weight polyisocyanate compounds are continuously hydrolyzed. A hydrolyzer 1 has the same configuration as that of FIG. 1. In the configuration shown in FIG. 4, no reservoir is provided and the target compound to be hydrolyzed is continuously supplied, taking into consideration that the distillation residues are continuously discharged from the chemical plant. There is no need of compressor. The apparatus includes a supplying pump 12 as a supplier, and a heater 13. In the case where the isocyanate target compound to be hydrolyzed such as distillation residue is introduced into the reactor 2 without being mixed with a solvent to a liquid state having low viscosity, the target compound is preferably heated at 120° C. or higher by the heater 13 to a melt state so that the target compound becomes flowable. In this case, however, if the target compound is heated at exceeding 180° C., there is a fear that the polymerization of the isocyanate target compound in the distillation residue is promoted. Therefore, it is preferable that the melt is at a temperature of 180° C. or lower, and more preferably 130 to 170° C. when introduced into the reactor 2.

In this configuration, a vessel having an agitator may be provided on the upstream of the reactor 2. Into the vessel, an isocyanate target compound such as distillation residue is added with a solvent and stirred, and then is introduced into the reactor 2 in a solution state. In this case, used as a solvent is hydrocarbon halide such as dichlorobenzene and ether-type solvents such as diethyleneglycoldiethylether, and these may be used alone or in mixture thereof. The solvent is used in an appropriate amount for rendering the isocyanate target compound flowable. In order to promptly obtain a uniform solution, it is preferable to provide a heater to the vessel having agitator, and the target compound and a solvent are agitated while being heated. In this case, the heating temperature is at 180° C. or lower, and preferably 130° C. to 170° C.

In the case of treating the isocyanate target compound, the water temperature (reaction temperature) inside the reactor 2 is set at 190° C. to 300° C. More preferable water temperature is 200° C. to 290° C. The water temperature is preferably set to a temperature lower than the temperature of the case of treating polyurethane, in order to avoid that the isocyanate compound is heated and polymerized before being hydrolyzed. The reaction pressure is properly adjusted so that the hydrolysis is conducted within the aforementioned temperature. Preferable reaction pressure is 9.8 to 14.7 MPa (100 to 150 kg/cm$^2$). The preferable hydrolysis ratio inside the reactor 2 is 0.5 times or more the target compound. When the hydrolysis ratio is less than 0.5 times, there are some cases where sufficient flowability cannot be obtained. Taking hydrolyzing efficiency into consideration, it is preferable that hydrolysis ratio is 1.0 times or more. As the hydrolyzing and recycling apparatus of the present invention is capable of efficiently conducting hydrolysis, the upper limit of the hydrolysis ratio is 5.0 times the target compound to be hydrolyzed in the reactor 2, and there is no need to supply further amount of water. When the hydrolysis ratio exceeds 3.0 times, the hydrolyzing efficiency is saturated. Taking into consideration the energy load at the post-processing step, it is preferable that the hydrolysis ratio is 3.0 times or less.

The hydrolyzed reaction product is discharged from the reactor and is supplied to the post-processor 7. In the configuration of FIG. 4, the post-processor 7 includes a degassing device 8, a dewatering column 9, and a reduced-pressure distillation column 14. The hydrolyzed reaction product includes an amine compound, $CO_2$, water, heavy end, and in some cases HCl or by-products having chlorine groups (including chlorine in an ionic state). The degassing device removes $CO_2$, and then, the dewatering column 9 separates and removes water and $CO_2$. In this case, the liquid discharged from the degassing device 8 is introduced into the dewatering column 9 at 60° C. or higher, and more preferably 80° C. or higher. If the temperature is too low, a solid substance may be precipitated.

In the case where the target compound to be hydrolyzed is waste from a chemical plant in which isocyanate compounds are industrially synthesized by a phosgene method, the hydrolyzed reaction product includes HCl or a compound having chlorine groups. In this case, care should be taken in determining temperature conditions in the dewatering column 9. If the dewatering is conducted at too high temperature, an amine compound obtained by hydrolysis is further decomposed by reacting HCl or chlorine groups, resulting in low recovering rate of amine compound. Such a decomposition of amine compound rarely occurs in the reactor 2 because water is present in the reactor 2 and hydrolysis predominatingly occurs. However, when the amount of water is decreased during the dewatering, the concentration of HCl or chlorine groups is relatively increased with respect to the amine compound, and as a result, the decomposition of amine compound easily occurs. Due to this reason, it is recommended to set the dewatering temperature in the dewatering column 9 to 240° C. or lower, and preferably 220° C. or lower, and more preferably 200° C. or lower, and the most preferably 180° C. or lower. There is no need of determining the upper limit of the dewatering temperature in the case where the target compound to be hydrolyzed includes almost no HCl and chlorine groups, or the case where the product to be recovered is a compound which does not react with HCl and chlorine groups to cause decomposition.

The liquid discharged after dewatering is purified in the reduced-pressure distillation column 14 to recover the amine compound. As there is a possibility that the amine compound reacts with HCl and chlorine groups in the reduced-pressure distillation column 14, it is necessary to control the temperature conditions in order to prevent recovering rate of amine compound from lowering. When the target compound to be hydrolyzed includes almost no HCl and chlorine groups, and the case where the product to be recovered is a compound which does not react with HCl and chlorine groups to cause decomosition, there is no need of determining the upper limit of the distillation temperature. The reduced-pressure conditions can be determined in accordance with the temperature conditions.

The post-processor 7 may be configured so that the reduced-pressure distillation column 14 is not included. In this case, a non-purified product discharged from the dewatering column 9 is recovered and is transferred to any other place where the non-purified product is purified to obtain a purified amine compound using known distillation column or other purifiers.

EXAMPLES

The present invention will be explained more specifically by way of examples. It is to be noted that the examples are for the explanatory purpose only and the present invention is not restricted to the examples.

Example 1

A polyurethane soft foam (apparent density before compression: 19.5 kg/m$^3$) synthesized from trylenediisocyanate (TDI) and polyetherpolyol (trifunctional; molecular weight of 3000) was hydrolyzed. First, an experiment for examining compression conditions was conducted using a compressor having a heater. Table 1 shows the heating temperature and the compression time, and the density of compressed product.

TABLE 1

| Heating and compression temperature (° C.) | Compression time (min.) | Density of compressed product (kg/m$^3$) |
|---|---|---|
| 160 | 5 | 450 |
| 150 | 5 | 410 |
| 140 | 5 | 330 |
| 140 | 15 | 450 |
| 120 | 30 | 450 |

As is obvious from Table 1, it is understood that, when the compression was conducted at a temperature as high as 150 to 160° C., the polyurethane soft foam was compressed to a density of 400 kg/m$^3$ or more (about 20 times) in about 5 minutes. In addition, it is understood that, even when the compression was conducted at a temperature as low as 120° C., the polyurethane soft foam was compressed to an increased density in about 30 minutes.

The compressed polyurethane resin was introduced into a reactor and was hydrolyzed and recovered under the conditions shown in Table 2. The reaction time was 30 minutes. As a result of hydrolysis, obtained were trylenediamine (TDA) derived from TDI and polyol. The results of experiments including the recovering rate of TDA (weight %), the recovering rate of polyol (weight %), and the hydrolyzing rate of polyurethane resin (weight %) are shown in Table 2 and FIG. 5.

The hydrolyzing rate of polyurethane resin shown in Table 2 was obtained from the following calculation:

$$\text{The hydrolyzing rate of urethane (\%)} = 100 \times \left(1 - \frac{\text{the remaining amount of urethane bond after hydrolysis}}{\text{the amount of urethane bond before hydrolysis}}\right)$$

The recovering rate of TDA (weight %) indicates the amount of TDA actually recovered with respect to the theoretical amount of TDA obtained based on the assumption that all the amount of TDI in the polyurethane foam introduced into the reactor is recovered as TDA. Same definition is applied for the recovering rate of polyol.

TABLE 2

| | Experiment No. | | | | | | |
|---|---|---|---|---|---|---|---|
| | 1 | 2 | 3 | 4 | 5 | 6 | 7 |
| Reaction temperature (° C.) | 200 | 250 | 270 | 318 | 320 | 340 | 370 |
| Pressure (MPa) | 10 | 10 | 20 | 20 | 20 | 20 | 20 |
| Hydrolysis ratio (weight) | 4 | 3 | 3 | 4 | 4 | 4 | 3 |
| TDA recovering rate (weight %) | 54.0 | 94.2 | 99.0 | 98.8 | 98.5 | 97.6 | 21.8 |
| Polyol recovering rate (weight %) | 21.0 | 84.2 | 94.5 | 99.0 | 97.3 | 93.4 | 13.1 |
| Polyurethane hydrolyzing rate (weight %) | 48.5 | 96.6 | 98.9 | 100 | 100 | 100 | 100 |

Figure 5:
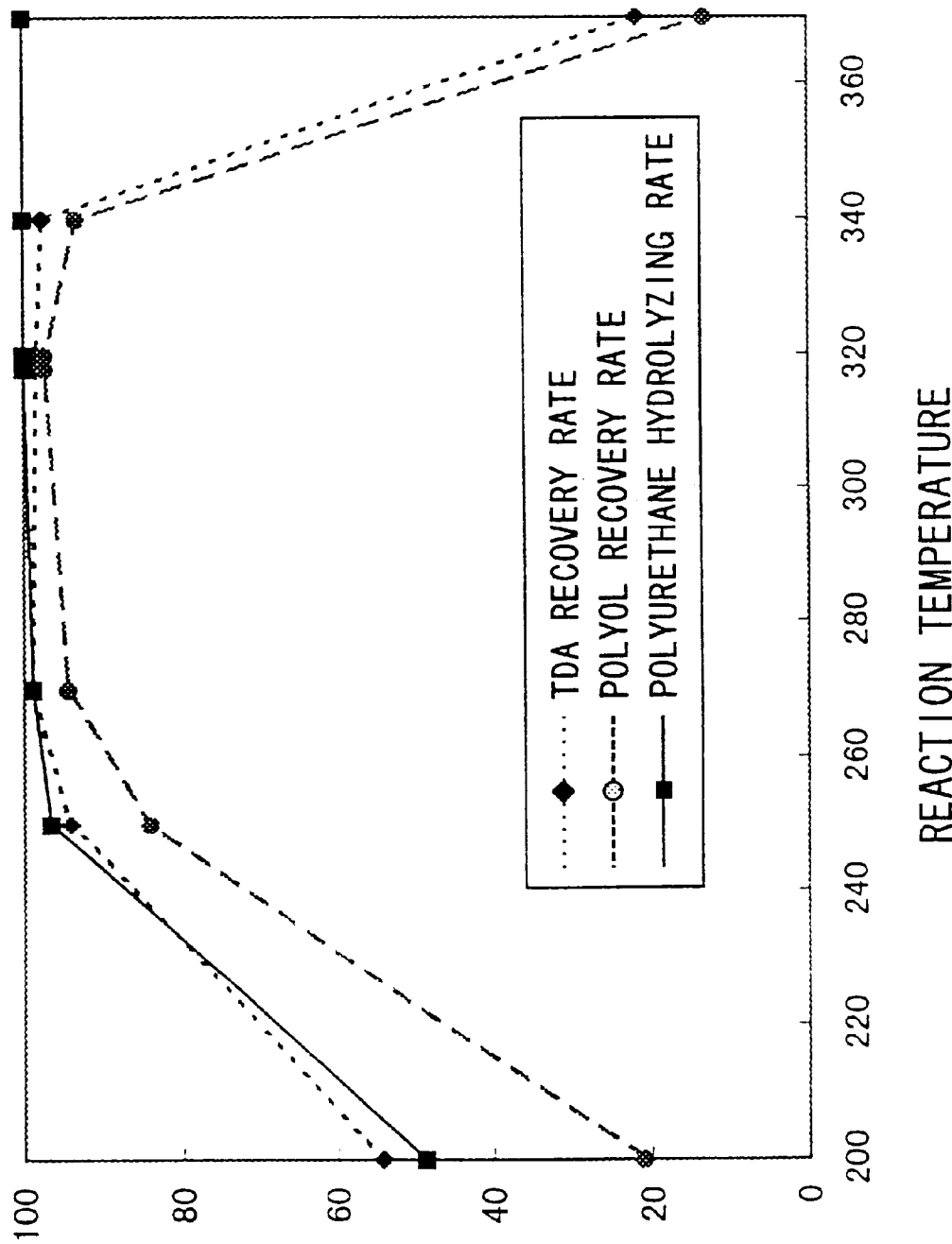
FIG. 5 is a graph illustrating an influence of the reaction temperature on the hydrolysis of polyurethane resin.

From Table 2 and FIG. 5, it is understood that the hydrolyzing rate and recovering rate were excellent at 250 to 340° C. At 370° C., whereas the polyurethane recovering rate was 100%, the recovering rate of TDA and polyol was poor. This is because the condensation of TDA and decomposition of polyol proceeded.

Example 2

A polyurethane hard foam (apparent density before compression: 36 kg/m$^3$) synthesized from polymeric MDI and polyetherpolyol (sorbitol type; hydroxyl value of 420 mg KOH/g) was hydrolyzed. As is the case of Example 1, an experiment for examining the compression conditions was conducted. Table 3 shows the heating temperature and compression time, and the density of compressed product.

TABLE 3

| Heating and compression temperature (° C.) | Compression time (min.) | Density of compressed product (kg/m³) |
|---|---|---|
| 180 | 5 | 700 |
| 170 | 5 | 700 |
| 160 | 10 | 700 |
| 150 | 15 | 570 |
| 140 | 30 | 700 |
| 140 | 60 | 700 |

As is obvious from Table 3, all the compressed products had a density as high as 700 kg/m³, except for the compressed product obtained at a temperature of 150° C. for 15 minutes.

The compressed polyurethane resin was introduced into the reactor, and was hydrolyzed at a reaction temperature of 240 to 255° C. and pressure of 10 MPa. The hydrolyzed reaction product was introduced into a separator and was dewatered. Then, the liquid discharged after dewatering was put into an autoclave, to which propylene oxide was sequentially added at 110° C. and 2.5 kg/cm² (0.245 MPa). As a result, polyol having hydroxyl value of 450 mg KOH/g and a viscosity of 20,000 Pa·s (25° C.) was obtained.

Example 3

Using distillation residue discharged in a chemical plant which synthesizes trylenediisocyanate (TDI), an experiment was conducted where the TDI residue was hydrolyzed to recover trylenediamine (TDA), which is an intermediate material of TDI. The distillation residue included about 10 weight % of TDI, and about 90 weight % of oligomers higher than dimer of TDI and the like. In Example 3, the same type of hydrolyzing and recycling apparatus shown in FIG. 4 was used.

Figure 6:
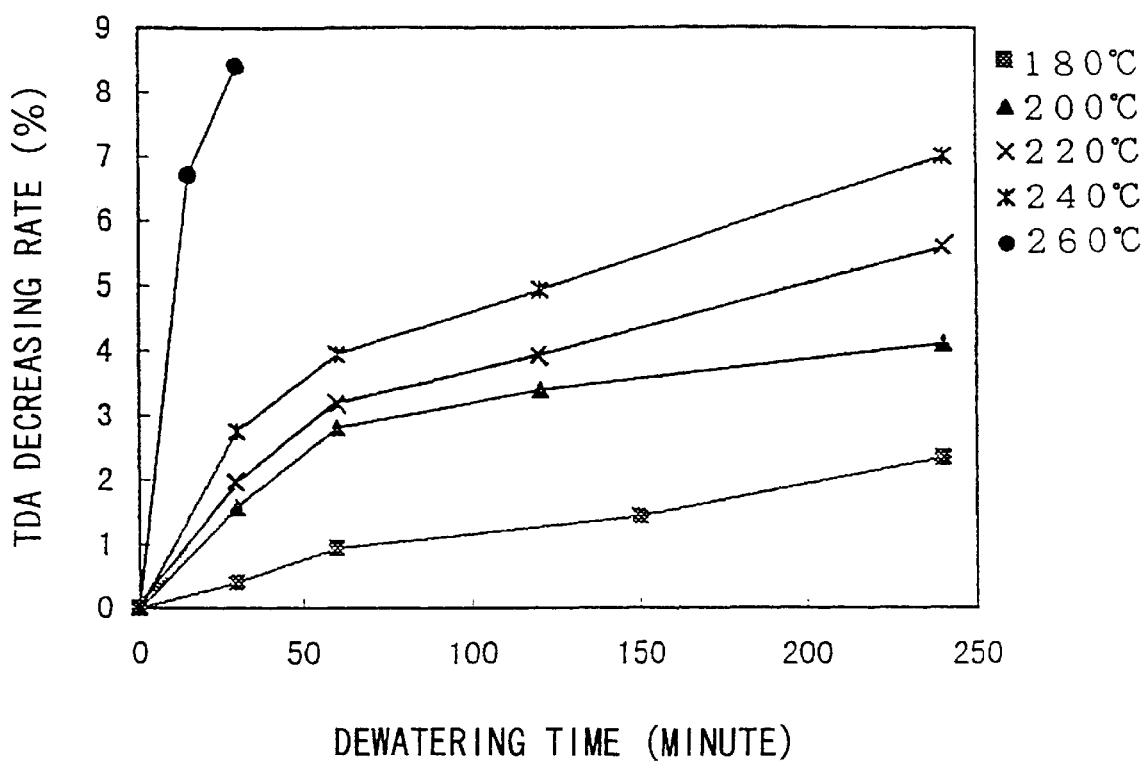
FIG. 6 is a graph illustrating an influence of the temperature on the bottom of dewatering tower and dewatering time on the decreasing rate of tolylenediamine.

The TDI residue was hydrolyzed in a reactor and then was introduced into the dewatering column, and experiments were performed as to the influence of the residence time inside the dewatering column and the temperature on the bottom of the column (a temperature measured on the bottom of the dewatering column) upon the decreasing rate of TDA (hydrolyzed TDI). The results of experiments are shown in FIG. 6. As is obvious from FIG. 6, as the dewatering was conducted at higher temperature, the decomposition of TDA by HCl or chlorine groups was promoted. Especially at 260° C., as the residence time in the column became longer, the decreasing rate of TDA sharply increased. Taking into consideration the time required for dewatering, it is found that the dewatering is advantageously conducted at 200° C. or lower where the decreasing rate of TDA is 5% or less even if the residence time is 240 minutes.

Example 4

Figure 7:
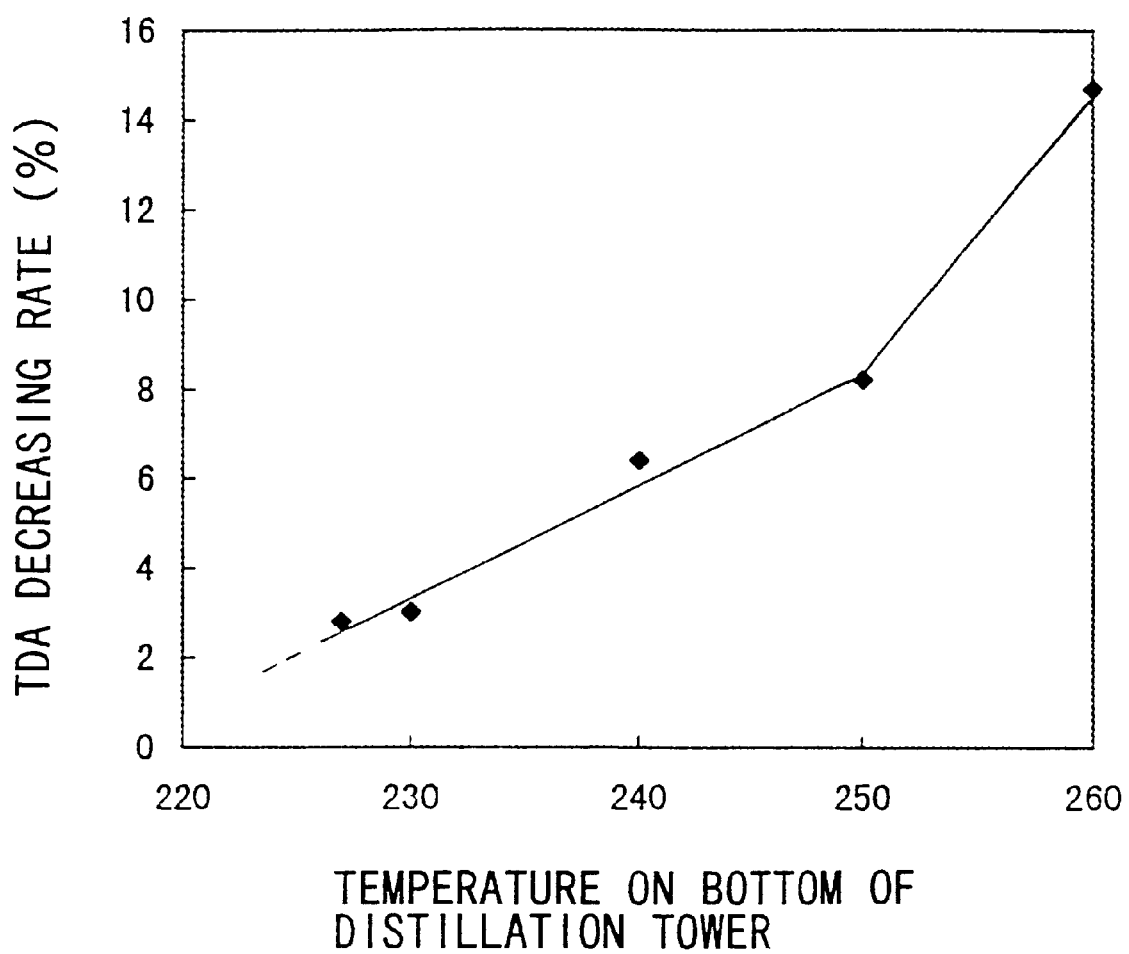
FIG. 7 is a graph illustrating an influence of the temperature on the bottom of distillation tower on the decreasing rate of tolylenediamine.

The same type of TDI residue as that used in Example 3 was hydrolyzed in a reactor to form a hydrolyzed reaction product, and then, was dewatered by a dewatering column. Using the liquid discharged after dewatering, the relationship between the distillation temperature and the decreasing rate of TDA by decomposition at a reduced-pressure distillation step was examined. The results of experiments are shown in Table 4 and FIG. 7.

TABLE 4

|  | Experiment No. 8 | Experiment No. 9 | Experiment No. 10 |
|---|---|---|---|
| Temperature on bottom of distillation column | 227 | 250 | 260 |
| All amount of feed (g) | 604 | 1197 | 683 |
| TDA amount (g) in feed | 495 | 989 | 609 |
| TDA amount discharged from top of column (g) | 443 | 886 | 400 |
| TDA amount on bottom of column (g) | 38.5 | 21.5 | 119.4 |
| Theoretical TDA remaining amount (g) | 52.3 | 102.7 | 209.2 |
| TDA decreasing rate (wt %) | 2.8 | 8.2 | 14.7 |

It is understood that as the distillation temperature becomes higher, the decreasing rate of TDA increases. Especially at the temperature exceeding 250° C., the decreasing rate sharply increases. From this result, it is preferable that the purifying (distilling) step for hydrolyzing and recovering TDA from TDI distillation residue is conducted at a temperature lower than 250° C., and more preferably 240° C. or lower, and the most preferably 230° C., taking into consideration the yield of TDA.

Example 5

Experiments were conducted where the TDI residue having the same composition of that used in Example 3 was hydrolyzed and recovered using the same type of apparatus as that shown in FIG. 4. As shown in Table 2, the hydrolysis conditions were varied. The TDA yield (the recovering rate of TDA) (%) of each experiment are shown in Table 5 and FIG. 8. The TDA yield (weight %) indicates the ratio of TDA (weight) actually recovered with respect to the theoretical amount of TDA (weight) obtained based on the assumption that all the distillation residue introduced into the reactor was TDI and all of TDI was recovered as TDA.

TABLE 5

| Experiment No. | Reaction temperature (° C.) | Reaction pressure (MPa) | Hydrolysis ratio* | TDA yield** (wt %) |
|---|---|---|---|---|
| 11 | 190 | 9.8 | 0.5 | 5 |
| 12 | 190 | 9.8 | 1.0 | 22 |
| 13 | 190 | 13.7 | 3.0 | 25 |
| 14 | 190 | 13.7 | 5.0 | 26 |
| 15 | 200 | 14.7 | 0.5 | 10 |
| 16 | 200 | 14.7 | 1.0 | 75 |
| 17 | 200 | 13.7 | 1.8 | 80 |
| 18 | 200 | 9.8 | 3.5 | 84 |
| 19 | 200 | 9.8 | 5.0 | 84 |
| 20 | 220 | 14.7 | 0.5 | 11 |
| 21 | 220 | 14.7 | 1.0 | 80 |
| 22 | 220 | 9.8 | 1.8 | 85 |
| 23 | 220 | 14.7 | 3.0 | 88 |
| 24 | 220 | 14.7 | 5.0 | 88 |
| 25 | 250 | 9.8 | 0.5 | 15 |
| 26 | 250 | 9.8 | 1.0 | 83 |

TABLE 5-continued

| Experiment No. | Reaction temperature (° C.) | Reaction pressure (MPa) | Hydrolysis ratio* | TDA yield** (wt %) |
|---|---|---|---|---|
| 27 | 250 | 14.7 | 1.8 | 97 |
| 28 | 250 | 14.7 | 3.0 | 100 |
| 29 | 250 | 13.7 | 3.5 | 100 |
| 30 | 250 | 13.7 | 5.0 | 100 |
| 31 | 270 | 9.8 | 0.5 | 14 |
| 32 | 270 | 9.8 | 1.0 | 78 |
| 33 | 270 | 14.7 | 1.8 | 85 |
| 34 | 270 | 9.8 | 3.0 | 87 |
| 35 | 270 | 9.8 | 5.0 | 86 |
| 36 | 290 | 14.7 | 0.5 | 12 |
| 37 | 290 | 14.7 | 1.0 | 60 |
| 38 | 290 | 14.7 | 1.8 | 68 |
| 39 | 290 | 14.7 | 3.0 | 69 |
| 40 | 290 | 14.7 | 5.0 | 69 |
| 41 | 300 | 14.7 | 0.5 | 5 |
| 42 | 300 | 14.7 | 1.0 | 25 |
| 43 | 300 | 14.7 | 1.8 | 31 |
| 44 | 300 | 14.7 | 3.0 | 32 |
| 45 | 300 | 14.7 | 5.0 | 31 |

*"Hydrolysis ratio" is high pressure and high temperature water weight/target compound to be hydrolyzed weight.

$$**\text{TDA yield} = \frac{\text{recovered TDA amount (g)} \times 100}{\text{theoretical recovered TDA amount (g)}}$$

assuming that all the TDI residue is TDI

Figure 8:
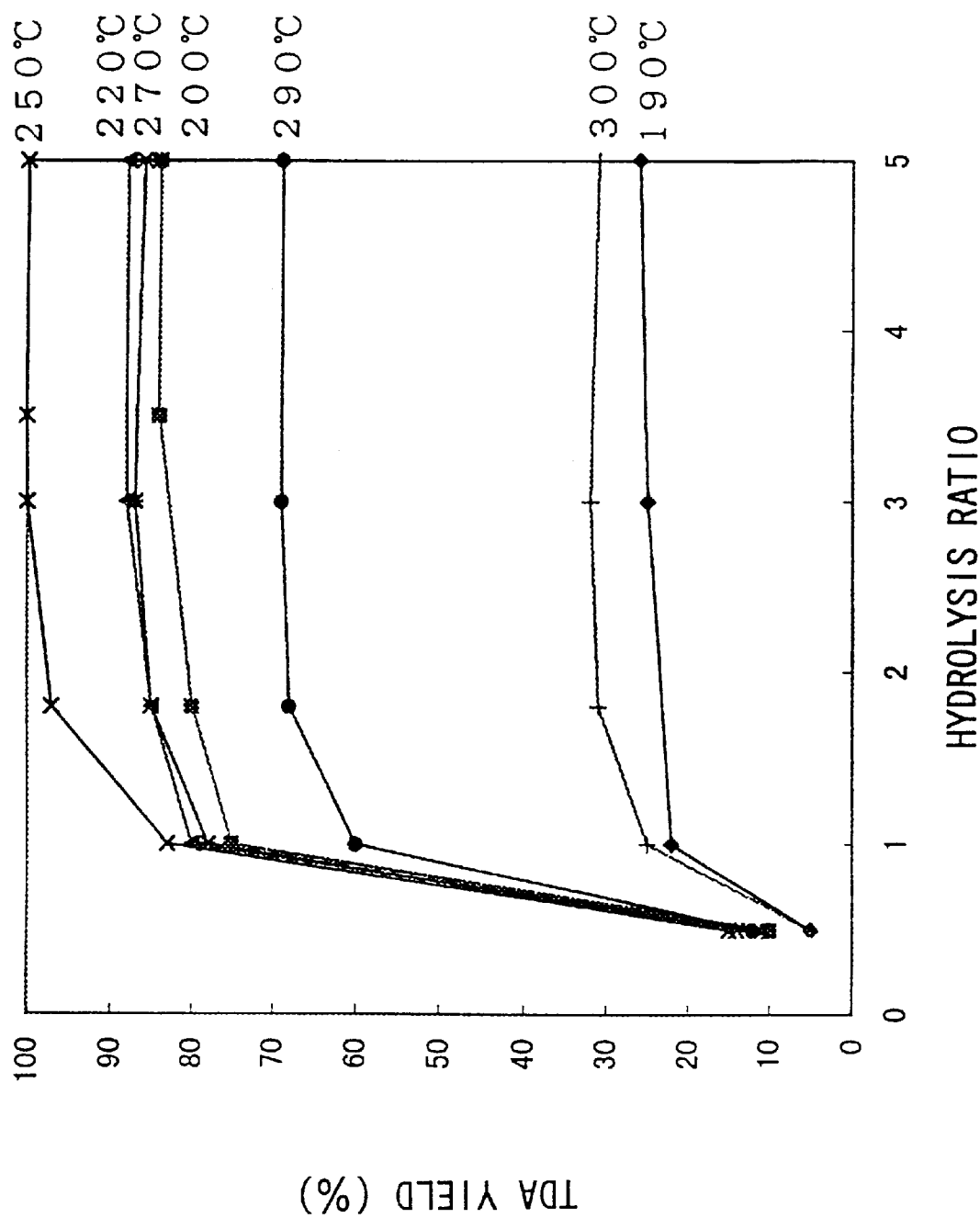
FIG. 8 is a graph illustrating an influence of the temperature inside the reactor and the hydrolysis ratio on the recycling rate of tolylenediamine.

From Table 5 and FIG. 8, TDA was recovered at each temperature when the hydrolysis ratio was 0.5 times or more. When the hydrolysis ratio was 1.0 time or more and the reaction temperature was 190 to 300° C., 20 weight % or more of TDA was recovered. Especially, at the reaction temperature of 200 to 290° C., 70 weight % or more of TDA was recovered, and at about 250° C., the recovering rate was 100 weight %. It is understood that the hydrolysis is largely influenced by temperature, and at hydrolysis ratio exceeding 3.0 times, the increase in recovering rate is saturated even at the same temperature. Experiments where the hydrolysis ratio was varied from 0.5 to 5.0 times at 180° C. and 9.8 MPa, and experiments where the hydrolysis ratio was varied from 0.5 to 5.0 times at 310° C. and 14.7 MPa were conducted. In both the experiments, the recovering rate of TDA was 5 weight % or less.

When the TDI residue having the same composition of those used in these experiments was merely distilled at 250° C., oligomers were decomposed and about 40 weight % of TDI could be recovered. However, according to the present invention, TDI and oligomers of TDI can be recovered as TDA in high yield, and the obtained TDA can be utilized as an intermediate material for synthesizing TDI. From this fact, the present invention is obviously advantageous.

After hydrolysis, the hydrolyzed reaction product from the reactor was supplied to the dewatering column where $CO_2$ and water were removed at a pressure of 0.95 kg/cm² (0.093 MPa) or less, and the temperature of 75° C. at the top of dewatering column and the temperature of 160° C. on the bottom of dewatering column. Then, the resultant was subjected to reduced-pressure distillation in the distillation column at a pressure of 0.027 kg/cm² (0.0026 MPa) and the temperature of 100° C. at the top of the distillation column and the temperature of 230° C. on the bottom of the distillation column. As a result of dewatering and distillation, about 90 weight % or more of TDA could be recovered from the TDA contained in the hydrolyzed reaction product.

Reference Example 1

The TDI residue having the same composition as that used in Example 3 was mixed with dichlorobenzene at a weight ratio of 1:1 to a solution state. Then, the solution was brought into contact with water at a temperature of 250° C. and a pressure of 10 kg/cm² (14.7 MPa) at a hydrolysis ratio of 1.8 to cause hydrolysis. The TDA yield was 90 weight %.

Reference Example 2

An experiment of hydrolysis was conducted using monomeric MDI (diphenylmethanediisocyanate) as a target compound to be hydrolyzed. As MDI is in a solid state at room temperature, the MDI was heated to a molten state. The molten MDI was continuously supplied to the reactor, and then, water at a temperature of 250° C. and a pressure of 150 kg/cm² (14.7 MPa) was continuously supplied thereto at a hydrolysis ratio of 1.8 to cause hydrolysis. The yield of MDA was 99 weight %. From this result, it is understood that MDA can be recovered as MDA at high yield.

INDUSTRIAL APPLICABILITY

According to the hydrolyzing and recycling apparatus and process of the present invention, the target compounds, polyisocyanate derivatives, such as polyurethane resins and low molecular weight polyisocyanate compounds can be recovered as a raw material or an intermediate material (derivatives) used for producing the target compounds. The apparatus of the present invention is capable of continuously hydrolyzing the target compound to be hydrolyzed. With this construction, the target compounds, which are discharged from a chemical plant as wastes in a molten state or in a solution state, can be continuously treated at constant conditions.

In addition, as the apparatus of the present invention is capable of recover polymer such as the polyurethane resins as polyol and polyamine, the apparatus of the present invention contributes to the promotion of recycling. Furthermore, as the optimum dewatering conditions and distillating conditions for recovering an amine compound from the low molecular weight polyisocyanate compounds have been successfully found, the amine compound can be recovered at high efficiency. The recovered amine compound can be effectively reused as a raw material for producing polyisocyanate compounds.

What is claimed is:

1. A process for hydrolyzing and recycling a polyurethane comprising:

supplying a target polyurethane compound to be hydrolyzed into a reactor;

bringing water at 190 to 370° C. and a pressure of 3 to 30 Mpa in liquid state into contact with the target compound in the reactor to hydrolyze said target compound; and post-processing a hydrolyzed reaction product discharged from the reactor.

2. The process of claim 1, wherein the polyurethane is continuously supplied to said reactor.

3. The process of claim 1, wherein said water is continuously supplied to said reactor.

4. The process of claim 1, comprising a plurality of reactors.

5. The process of claim 1, wherein said water is present in an amount of 1.0 to 10.0 times, by weight, of the target compound.

6. The process of claim 1, wherein the pressure of the water is at least 6 MPa.

7. The process of claim 1, wherein the pressure of the water is at most 25 MPa.

8. The process of claim 1, wherein the pressure of the water is at most 20 MPa.

9. The process of claim 1, wherein the temperature of the water is 200 to 370° C.

10. The process of claim 1, wherein the temperature of the water is at most 340° C.

11. The process of claim 1, wherein the temperature of the water is at least 250° C.

12. The process of claim 1, wherein polyol and/or polyamine compounds are recovered in said post-processing.

13. The process of claim 1, wherein said post-processing comprises dewatering.

14. The process of claim 1, wherein said post-processing comprises an addition reaction.

15. The process of claim 14, wherein said additional reaction comprises reaction with an alkylene oxide.

16. The process of claim 1, wherein said post-processing comprises distillation.

17. The process of claim 16, wherein said distillation comprises reduced pressure distillation.

18. The process of claim 1, wherein said post-processing comprises separation of the hydrolyzed reaction product.

19. The process of claim 18, wherein said separation comprises liquid separation.

20. The process of claim 1, wherein the target polyurethane compound is a pre-compressed polyurethane foam.

21. The process of claim 20, wherein said pre-compressed polyurethane foam is produced by heating 100 to 250° C.

* * * * *